(12) United States Patent
Meyer et al.

(10) Patent No.: US 8,211,972 B2
(45) Date of Patent: Jul. 3, 2012

(54) EMULSIFIER SYSTEMS FOR COSMETIC AND PHARMACEUTICAL OIL-IN-WATER EMULSIONS

(75) Inventors: Juergen Meyer, Essen (DE); Christian Hartung, Essen (DE); Karin Czech, Essen (DE); Michael Ferenz, Essen (DE); Andrea Lohse, Bottrop (DE); Sascha Herrwerth, Essen (DE); Frank Unger, Duisburg (DE); Burghard Gruening, Essen (DE)

(73) Assignee: Evonik Goldschmidt GmbH, Essen (DE)

( * ) Notice: Subject to any disclaimer, the term of this patent is extended or adjusted under 35 U.S.C. 154(b) by 227 days.

(21) Appl. No.: 12/558,005

(22) Filed: Sep. 11, 2009

(65) Prior Publication Data

US 2010/0081763 A1 Apr. 1, 2010

(30) Foreign Application Priority Data

Sep. 26, 2008 (DE) .......................... 10 2008 042 381

(51) Int. Cl.
*C08L 83/12* (2006.01)
(52) U.S. Cl. ....................................... 524/588; 556/445
(58) Field of Classification Search .................. 524/588; 556/445
See application file for complete search history.

(56) References Cited

U.S. PATENT DOCUMENTS

| | | | |
|---|---|---|---|
| 3,715,334 A | 2/1973 | Karstedt | |
| 3,775,452 A | 11/1973 | Karstedt | |
| 4,698,178 A | 10/1987 | Huttinger et al. | |
| 5,500,254 A * | 3/1996 | Quincy et al. ................. | 427/387 |
| 6,288,129 B1 | 9/2001 | Gruning et al. | |
| 7,319,120 B2 | 1/2008 | Herzig et al. | |
| 7,361,777 B2 | 4/2008 | Herrwerth et al. | |
| 7,442,666 B2 | 10/2008 | Herrwerth et al. | |
| 2005/0136269 A1 | 6/2005 | Doehler et al. | |
| 2006/0155089 A1 | 7/2006 | Ferenz et al. | |
| 2006/0155090 A1 | 7/2006 | Ferenz | |
| 2006/0188455 A1 | 8/2006 | Ferenz et al. | |
| 2006/0188456 A1 | 8/2006 | Ferenz et al. | |
| 2006/0204468 A1 | 9/2006 | Allef et al. | |
| 2007/0100153 A1 | 5/2007 | Brueckner et al. | |
| 2007/0128143 A1 | 6/2007 | Gruning et al. | |
| 2007/0184006 A1 | 8/2007 | Ferenz et al. | |
| 2008/0027202 A1 | 1/2008 | Ferenz et al. | |
| 2008/0216708 A1 | 9/2008 | Herrwerth et al. | |
| 2008/0305065 A1 | 12/2008 | Ferenz et al. | |
| 2009/0007483 A1 | 1/2009 | Hansel et al. | |
| 2009/0062459 A1 | 3/2009 | Thum et al. | |
| 2009/0087399 A1 | 4/2009 | Kuppert et al. | |
| 2009/0093598 A1 | 4/2009 | Venzmer et al. | |

FOREIGN PATENT DOCUMENTS

| | | |
|---|---|---|
| DE | 2646726 C2 | 1/1983 |
| DE | 102005001039 A1 | 7/2006 |
| DE | 102005001041 A1 | 7/2006 |
| EP | 1125574 B1 | 6/2005 |
| EP | 1520870 B1 | 1/2006 |
| EP | 1754740 A2 | 2/2007 |
| EP | 1439200 B1 | 6/2007 |

OTHER PUBLICATIONS

U.S. Appl. No. 12/536,146 entitled, "Use of Polysiloxanes with Quaternary Ammonium Groups for Protecting Animal or Human Hair Against Heat Damange", filed on Aug. 5, 2009, first name inventor: Sascha Herrwerth.
U.S. Appl. No. 12/547,109 entitled, "Process for Preparing Branched Si-H Functional Polysiloxanes and Use Thereof for Preparing Liquid SiC-Linked, Branched Modified Organomodified Polysiloxanes" filed on Aug. 25, 2009, first name inventor: Frauke Henning.

* cited by examiner

*Primary Examiner* — Kuo-Liang Peng
(74) *Attorney, Agent, or Firm* — Scully, Scott, Murphy & Presser, P.C.

(57) ABSTRACT

The invention relates to emulsifier systems for cosmetic and pharmaceutical oil-in-water emulsions comprising high molecular weight organomodified polysiloxanes with a dispersion index greater than 1.6.

9 Claims, No Drawings

EMULSIFIER SYSTEMS FOR COSMETIC AND PHARMACEUTICAL OIL-IN-WATER EMULSIONS

FIELD OF THE INVENTION

The invention relates to emulsifier systems for cosmetic and pharmaceutical oil-in-water emulsions comprising high molecular weight organomodified polysiloxanes with a polydispersity greater than 1.6. The present invention also relates to cosmetic and pharmaceutical oil-in-water emulsions and to cosmetic and pharmaceutical compositions.

BACKGROUND OF THE INVENTION

Organomodified siloxanes are used in a wide variety of applications. Their properties can be adjusted in a targeted manner, inter alia by the type of modification, and also by the modification density.

Thus, for example, allyl polyethers can be attached to a siloxane backbone, thereby providing organophilic or non-ionic hydrophilic modifications. Compounds of this type are used, for example, as polyurethane foam stabilizers, as defoamers in fuels or as additives in paints and coatings.

DE 102005001041 describes functionalized polyorganosiloxanes and their use as fuel defoamers. The allyl polyethers in the siloxanes presented therein can, if appropriate, be replaced by hydrocarbon radicals by modifying the synthesis.

In general, siloxanes can be linked with hydrophobic groups by reacting with, for example, α-olefins. The silicone waxes obtained in this way serve, for example, as an additive in personal care applications.

It is found in many fields of application that the effect of the siloxane depends decisively on the compatibility with the corresponding formulation.

Suitable cosmetic emulsifiers are, for example, siloxanes which, besides aliphatic groups based on α-olefins, carry polyethers. A typical example to be mentioned here is the commercial product ABIL EM 90 from Evonik Goldschmidt GmbH (Germany), which is characterized in particular by excellent stabilization of water-in-oil (W/O) emulsions (see U.S. Pat. No. 4,698,178).

Siloxane-based emulsifiers for oil-in-water (O/W) emulsions need to have a relatively hydrophilic character, for which reason these products are usually pure polyethersiloxanes.

EP 1125574 describes the use of relatively hydrophobic polyethersiloxanes as O/W emulsifiers in which the polyether groups are in α,ω-position of the siloxane backbone. These structures are characterized in particular by a velvety-silky skin feel which they are able to incorporate into cosmetic emulsions.

Disadvantages of using these structures are the often inadequate emulsion stabilization and also the complex production on account of the demanding topology.

SUMMARY OF THE INVENTION

In general, the present invention provides emulsifier systems which are able to achieve a velvety-silky skin feel and at the same time give high emulsion stabilization.

Surprisingly, it has been found that high molecular weight organomodified siloxanes or mixtures of different high molecular weight organomodified siloxanes act as emulsifying components and, in conjunction with a good skin feel produce particularly stable oil-in-water emulsions if they have an unusually broad molecular weight distribution.

Surprisingly, in the case of high molecular weight polyethersiloxanes with a broad molecular weight distribution, even a relatively low degree of substitution with hydrophilic polyether groups is able to achieve excellent emulsifying performance, while simultaneously achieving a velvety-silky skin feel.

Specifically, the present invention provides emulsifier systems for cosmetic and pharmaceutical oil-in-water emulsions comprising high molecular weight organomodified polysiloxanes with a polydispersity D greater than 1.6.

DETAILED DESCRIPTION OF THE INVENTION

The organomodified polysiloxanes or polyethersiloxane mixtures according to the invention are described below by way of example without any intention of limiting the invention to these exemplary embodiments. Where ranges, general formulae or compound classes are given below, then these are intended to encompass not only the corresponding ranges or groups of compounds explicitly mentioned, but also all partial ranges and partial groups of compounds which can be obtained by removing individual values (ranges) or compounds. Where documents are cited within the context of the present description, then it is intended for their content, in its entirety, to form part of the disclosure of the present invention. If, within the context of the present invention, compounds such as, for example, organomodified polysiloxanes are described which can have different units a number of times, then these may occur in these compounds in random distribution (random oligomer) or arranged (block oligomer). Data relating to the number of units in such compounds is to be understood as meaning the average value, averaged over all of the corresponding compounds. Unless stated otherwise, all of the stated per cent (%) are per cent by mass.

As stated above, the present invention provides emulsifier systems for cosmetic and pharmaceutical oil-in-water emulsions comprising high molecular weight organomodified polysiloxanes with a polydispersity D greater than 1.6.

The polydispersity D is the quotient of the weight-average Mw and the number-average Mn of the molecular weight distribution of the polysiloxanes. The polydispersity is a recognized measure of the width of a molecular mass distribution. Polysiloxanes typically have a polydispersity D of less than 1.6.

A customary method of ascertaining the molecular weight distribution is gel permeation chromatography (GPC).

The GPC method used in the present application is analogous to the standard DIN 55072-1/ISO 13885-1. The GPC data were obtained on a Hewlett Packard HP 1100 instrument with HP RI detector and the following parameters:

| | |
|---|---|
| Column: | SDV1000/10000 Å, length: 65.00 cm, internal diameter: 0.80 cm, temperature: 30° C. |
| Mobile phase: | THF |
| Flow rate: | 1.00 ml/min |
| Sample concentration: | 10.00 g/l |
| Calibration: | against PS [162-2 057 000 g/mol]. |

To evaluate the chromatograms, the evaluation software WinGPC Unity from Polymer Standards Service, Mainz, Germany, was used.

For the present data, only the product signal in the GPC chromatogram was taken into consideration. If the polysiloxanes are polyethersiloxanes which have been prepared by means of hydrosilylation, these usually comprise a certain fraction of free polyether as a secondary constituent. In the GPC, these free polyether fractions give signals which may superimpose the product peak. Accordingly, a standard multipeak evaluation analogous to HPLC evaluations was used, and only the product signal (organomodified polysiloxane) was taken into consideration. If other signals at relatively low molecular masses have superimposed this product signal, the minimum between the signals was determined using the evaluation software, a drop to the baseline was carried out and the chromatogram evaluated only above the molecular weight of the minimum.

The polydispersity D of the polysiloxanes used in the emulsifier system according to the invention is greater than 1.6, preferably greater than 1.7 and particularly preferably greater than 1.8 (determined for the product signal according to the GPC method explained above).

Within the context of the present invention, "high molecular weight polysiloxanes" are understood as meaning polysiloxanes which have a weight average Mw of at least 5000 g/mol, preferably of at least 10 000 g/mol and particularly preferably of 15 000 g/mol (determined for the product signal according to the GPC method explained above).

The emulsifier systems according to the invention may be an individual organomodified polysiloxane with a broad molecular weight distribution, or mixtures of organomodified polysiloxanes of different molecular weight distributions.

Polysiloxanes with a widely distributed molecular weight distribution which additionally comprise significant high molecular weight fractions are particularly advantageous.

Thus, in the emulsifier system according to the invention, preference is given to using polysiloxanes which have a fraction of polysiloxanes with a molecular weight of $\geq 1*10^4$ g/mol of above 75%, preferably of above 80% and particularly preferably of above 85%, based on the total amount of the polysiloxane.

Particular preference is given here to emulsifier systems comprising polysiloxanes with a fraction of polysiloxanes with a molecular weight of $\geq 1*10^5$ g/mol of above 2%, preferably of above 2.5% and particularly preferably of above 5%, based on the total amount of the polysiloxane.

A too high molecular weight of the polysiloxane used in the emulsifier system according to the invention can have adverse effects on the emulsifying performance, thus in the emulsifier system according to the invention, preference is given to using polysiloxanes which have a fraction of polysiloxanes with a molecular weight of $\geq 1*10^7$ g/mol of less than 5%, preferably of less than 2% and particularly preferably of less than 1%, based on the total amount of the polysiloxane.

The fraction of the polysiloxanes of a certain molecular weight is determined via the particular area fractions of the respective polysiloxane of a certain molecular weight according to the GPC method explained above. The area fraction is based on the area of all polysiloxanes (=total amount of polysiloxane); thus, the % quoted here are area %.

Preferred emulsifier systems of the invention comprise at least one polyethersiloxane.

Preferred emulsifier systems used in the present invention comprise polyethersiloxane of the general formula I $$M_{2+c+2d}D_a D'_b T_c Q_d \qquad \text{formula I,}$$

where
$M=(R^1 R^2_2 SiO_{1/2})$
$D=(R^2_2 SiO_{2/2})$
$D'=(R^2 R^3 SiO_{2/2})$
$T=(R^2 SiO_{3/2})$
$Q=(SiO_{4/2})$ a=30-800, preferably 40-50, in particular 50-400,
b=1-15, preferably 3-10, in particular 4-8,
c=0-2, preferably 0-1, in particular 0,
d=0-2, preferably 0-1, in particular 0,
$R^1=R^2$ or $R^3$,
$R^2$=independently of one another, identical or different linear or branched, optionally aromatic hydrocarbon radicals having 1 to 16 carbon atoms, which optionally carry OH or ester functions, preferably methyl or phenyl, in particular methyl,
$R^3$=independently of one another, identical or different polyether radicals of the general formula II $$-CH_2-CH_2-(CH_2)_n O(EO)_x(PO)_y(XO)_z R^4 \qquad \text{formula II,}$$

where
$EO=(C_2H_4O)$
$PO=(C_3H_6O)$
$XO=(C_2H_3R^5O)$
n=1-9, in particular 1
x=2-50, in particular 10-30
y=0-50, in particular 2-15
z=0-10, in particular 0
$R^4$=independently of one another, identical or different radicals selected from the group comprising: H, alkyl radicals having 1 to 16 carbon atoms, or carboxylate radicals, preferably H or methyl, and
$R^5$=independently of one another, identical or different radicals selected from the group comprising: alkyl radicals having 2 to 16 carbon atoms, which are optionally interrupted by ether functions, alkaryl radicals having 7-18 carbon atoms, aryl radicals having 6 to 16 carbon atoms, preferably ethyl or phenyl.

The compounds are in the form of a mixture with a distribution controlled essentially by laws of statistics. The values for the indices x, y and z are therefore average values. The units characterized with the indices X, y and z can be present in the compounds of the formula II in random distribution, blockwise or arranged in any other desired order.

In the emulsifier systems according to the invention it is possible to use polyethersiloxanes with relatively hydrophilic polyethers without adversely affecting the velvety-silky skin feel of the emulsifier systems in cosmetic and dermatological formulations. At the same time, however, such molecules are characterized by a particularly good emulsion stabilization.

Emulsifier systems according to the invention therefore preferably comprise polyethersiloxanes with a high EO fraction for whose polyether component according to formula II the following applies:

$$x/(y+z)>1, \text{ preferably } >2 \text{ and particularly preferably } >3.$$

It may be advantageous for the emulsifying properties and the skin feel if the fraction of unmodified D units in the polyethersiloxanes used is significantly greater than the fraction of modified D' units.

Emulsifier systems according to the invention thus preferably comprise polyethersiloxanes which are characterized in that the ratio a/b (from formula I) is >5, preferably >8 and particularly preferably >10.

It may be particularly advantageous for the skin feel if polyethersiloxanes with a relatively low polyether fraction are used.

Emulsifier systems according to the invention therefore preferably comprise polyethersiloxanes of the general formula I which, on average, comprise at least three polyether radicals and in which the maximum number of polyether radicals $R^3$ bonded to the molecule is <a/5.

Polyethersiloxanes for use in the emulsifier systems according to the invention are accessible in various ways. In general, they are obtained by hydrosilylation of allyl-functional polyethers with SiH-functional siloxanes. Compounds of this type are described, for example, in EP 1754740.

The parent SiH-functional siloxanes are generally obtained by the equilibration of various basic siloxane units. Processes for the equilibration are described, for example, in the patent specifications EP 1439200 and DE 102005001039, to which reference is expressly made and which are thus part of the disclosure of the present application. On an industrial scale, to synthesize SiH-group-carrying organopolysiloxanes, preferably readily accessible siloxane compounds, such as, for example, decamethylcyclopentasiloxane, poly(methylhydrogen)siloxanes, 1,1,3,3-tetramethyldisiloxane or hexamethyldisiloxane, are reacted in the presence of a suitable catalyst. Suitable catalysts are strong acids, such as trifluoromethanesulphonic acid. In the process, the corresponding equilibrates are formed. The SiH functionalities can be present, depending on the catalyst used, in random distribution over the siloxane main chain, or else may occur blockwise. The degree of functionality of the individual polymer molecules is also subject to a distribution. The indices a, b, c and d of the siloxanes used in the context of this invention are therefore average values. The units characterized with the indices a, b, c and d can be present in the compounds of the formula I in random distribution, blockwise or arranged in any other desired order.

The catalyst used for the hydrosilylation reaction is in particular platinum and its compounds. In this connection, the platinum is used either in metallic form, as metal fixed to a support or in the form of an optionally soluble platinum complex. Until now, a large part of the hydrosilylation reactions carried out industrially have been used the so-called Karstedt catalyst known from U.S. Pat. Nos. 3,715,334 and 3,775,452.

The synthesis of the polyethersiloxanes according to the invention can take place without a solvent. In some circumstances, however, the use of a solvent is advantageous or necessary. The polyethers are generally incompatible with the siloxane and by using a solvent it is possible to avoid the initiation of the reaction being delayed.

The technical reaction procedure for preparing the polyethersiloxanes can influence the properties of the product, especially if a plurality of different polyether radicals is added. Products according to the invention can be prepared, inter alia, either in discontinuously, semi-continuously or continuously operated vessels.

Suitable processes for the hydrosilylation are described, for example, in the book "Chemie und Technologie der Silicone [Chemistry and Technology of Silicones]", Verlag Chemie, 1960, page 43, and in DE 2646726, U.S. Pat. No. 3,775,452 and EP 1520870, to which reference is expressly made.

For the preparation of the polyethersiloxanes according to the invention it is possible to use various polyethers. These polyethers are generally prepared by the addition reaction of epoxides with mono- or polyfunctional alcohols or an amine. On account of their good commercial availability, epoxides which are particularly suited for the synthesis of polyethers are: ethylene oxide, propylene oxide, butylene oxide or styrene oxide.

If different monomers are used for the preparation of the polyethers, for example in order to adjust the hydrophilicity of the product in a targeted manner, then it is possible, by means of the order of the metered addition and by means of the adjustment of various reaction parameters, to control the distribution of the monomer units along the polymer main chain so that, for example, different monomer units can arise blockwise or be present in gradual and/or random distribution.

Polyethers which can also be used are those polyethers which have been further modified by the process of graft polymerization. For this, the polyethers are reacted with monomers carrying double bonds in the presence of free-radical activators. By adjusting the degree of grafting and the amount and type of the monomers used and/or by means of the method of preparing the copolymers, it is possible to modify the properties of the polyethers in a targeted manner. Suitable monomers are, for example, methyl methacrylate, styrene or maleic anhydride.

The polysiloxanes obtained by these processes typically have molecular weight distributions with a polydispersity of $D<1.6$.

Most easily, a broadening of the molecular weight distribution can be achieved by mixing together siloxanes with different average molecular weights.

The invention therefore provides an emulsifier system in which the polydispersity of the polysiloxane is adjusted by mixing polysiloxanes with differing molecular weights.

In addition, a broadening of the molecular weight distribution is also possible through a targeted crosslinking of the polyethersiloxanes. For example, this can be achieved by adding polyfunctional double-bond-containing substrates to the polyethers during the hydrosilylation, for example diallyl polyethers or divinylsiloxanes (U.S. Patent Application Publication No. 2006/0155090).

The invention therefore further provides an emulsifier system in which the polydispersity index D of the polysiloxane can be adjusted by using polyfunctional double-bond-containing substrates during the preparation of the polysiloxane in the course of the hydrosilylation.

A crosslinking for further broadening the molecular weight distribution is furthermore possible by reacting the polyethersiloxanes via the end groups of the polyethers with polyfunctional reactive substrates, such as isocyanates (see U.S. Pat. No. 7,319,120) or carboxylic anhydrides.

The invention therefore further provides an emulsifier system in which the polydispersity of the polyethersiloxane can be adjusted by reacting the polyethersiloxanes with polyfunctional reactive substrates via the end groups of the polyethers.

A combination of the different measures for broadening the molecular weight distribution is of course possible.

For the use of the emulsifier systems according to the invention in cosmetic applications, it is advantageous if these are liquid and pumpable at room temperature.

It is therefore advantageous to convert highly viscous emulsifier systems according to the invention into a pumpable, flowable form by adding suitable liquefying agents. Typically, pumpable systems of this type have a viscosity of $<10\,000$ mPas (at a shear rate of $10\ \text{s}^{-1}$ at $25°$ C.). These pumpable emulsifier systems containing liquefying agents are preferably clear to translucent-opaque.

Suitable liquefying agents which can be used are usually all types of cosmetic emollients. Cosmetic emollients which can be used are all cosmetic oils, in particular mono-or diesters of linear and/or branched mono- and/or dicarboxylic acids having 2 to 44 carbon atoms with linear and/or branched saturated or unsaturated alcohols having 1 to 22 carbon atoms. The esterification products of aliphatic, difunctional alcohols having 2 to 36 carbon atoms with monofunctional aliphatic carboxylic acids having 1 to 22 carbon atoms are also suitable. Also suitable are long-chain aryl acid esters, such as, for example, esters of benzoic acid, e.g., benzoic acid esters of linear or branched, saturated or unsaturated alcohols having 1 to 22 carbon atoms, or else isostearyl benzoate or octyldodecyl benzoate. Further monoesters suitable as emollients and oil components are, for example, the methyl esters and isopropyl esters of fatty acids having 12 to 22 carbon atoms, such as, for example, methyl laurate, methyl stearate, methyl oleate, methyl erucate, isopropyl palmitate, isopropyl myristate, isopropyl stearate, isopropyl oleate. Other suitable monoesters are, for example, n-butyl stearate, n-hexyl laurate, n-decyl oleate, isooctyl stearate, isononyl palmitate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate and also esters which are obtainable from technical-grade aliphatic alcohol cuts and technical-grade, aliphatic carboxylic acid mixtures, e.g., esters of unsaturated fatty alcohols having 12 to 22 carbon atoms and saturated and unsaturated fatty acids having 12 to 22 carbon atoms, as are accessible from animal and vegetable fats. Also suitable are naturally occurring monoester and/or wax ester mixtures as are present, for example, in jojoba oil or in sperm oil. Suitable dicarboxylic acid esters are, for example, di-n-butyl adipate, di-n-butyl sebacate, di(2-ethylhexyl)adipate, di(2-hexyldecyl)succinate, diisotridecyl azelate. Suitable diol esters are, for example, ethylene glycol dioleate, ethylene glycol diisotridecanoate, propylene glycol di(2-ethylhexanoate), butanediol diisostearate, butanediol dicaprylate/caprate and neopentyl glycol dicaprylate. Further substances which can be used as emollients are, for example, $C_{12-15}$ alkyl benzoate, dicaprylyl carbonate, di-2-ethylhexyl carbonate. Emollients and oil components which may likewise be used are relatively long-chain triglycerides, i.e., triple esters of glycerol with three acid molecules, of which at least one is relatively long-chained. Mention may be made here, by way of example, of fatty acid triglycerides; as such, it is possible to use, for example, natural, vegetable oils, e.g., olive oil, sunflower oil, soybean oil, peanut oil, rapeseed oil, almond oil, sesame oil, avocado oil, castor oil, cocoa butter, palm oil, but also the liquid fractions of coconut oil or of palm kernel oil and also animal oils, such as, for example, shark liver oil, cod liver oil, whale oil, beef tallow and butterfat, waxes such as beeswax, carnauba palm wax, spermaceti, lanolin and claw oil, the liquid fractions of beef tallow and also synthetic triglycerides of caprylic/capric acid mixtures, triglycerides of technical-grade oleic acid, triglycerides with isostearic acid, or from palmitic acid/oleic acid mixtures as emollients and oil components. Furthermore, hydrocarbons, in particular also liquid paraffins and isoparaffins, can be used. Examples of hydrocarbons which can be used are paraffin oil, isododecane, isohexadecane, polydecene, vaseline, Paraffinum Perliquidum, squalane, ceresine. Furthermore, it is also possible to use linear or branched fatty alcohols such as oleyl alcohol or octyldodecanol, and also fatty alcohol ethers such as dicaprylyl ether. Suitable silicone oils and silicone waxes are, for example, polydimethylsiloxanes, cyclomethylsiloxanes, and also aryl- or alkyl- or alkoxy-substituted polymethylsiloxanes or cyclomethylsiloxanes. Suitable further oils are, for example, Guerbet alcohols based on fatty alcohols having 6 to 18, preferably 8 to 10, carbon atoms, esters of linear $C_6$-$C_{22}$-fatty acids with linear $C_6$-$C_{22}$-fatty alcohols, esters of branched $C_6$-$C_{13}$-carboxylic acids with linear $C_6$-$C_{22}$-fatty alcohols, esters of linear $C_6$-$C_{22}$-fatty acids with branched $C_8$-$C_{18}$-alcohols, in particular 2-ethylhexanol or isononanol, esters of branched $C_6$-$C_{13}$-carboxylic acids with branched alcohols, in particular 2-ethylhexanol or isononanol, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, vegetable oils, branched primary alcohols, substituted cyclohexanes, linear $C_6$-$C_{22}$-fatty alcohol carbonates, Guerbet carbonates, esters of benzoic acid with linear and/or branched $C_6$-$C_{22}$-alcohols (e.g. Finsolv™ TN), dialkyl ethers, ring-opening products of epoxidized fatty acid esters with polyols, silicone oils and/or aliphatic or naphthenic hydrocarbons.

Emollients used as liquefiers are preferably mono- or diesters of linear and/or branched mono- and/or dicarboxylic acids having 2 to 44 carbon atoms with linear and/or branched saturated or unsaturated alcohols having 1 to 22 carbon atoms. Relatively long-chain triglycerides, i.e., triple esters of glycerol with three acid molecules, of which at least one is relatively long-chain (number of carbon atoms greater than 12) are also preferably used. Preference is likewise given to using branched and linear liquid hydrocarbons and also silicone oils as liquefying agents.

Hydrotropes can also be used as liquefying agents. Hydrotropes are, for example, ethanol, isopropyl alcohol or polyols. Polyols which are suitable here can have 2 to 15 carbon atoms and at least two hydroxyl groups. Typical examples are: glycerol, alkylene glycols, such as, for example, ethylene glycol, diethylene glycol, propylene glycol, butylene glycol, hexylene glycol and polyethylene glycols with an average molecular weight of from 100 to 1000 Daltons, technical-grade oligoglycerol mixtures with a degree of self-condensation of from 1.5 to 10, such as, for example, technical-grade diglycerol mixtures with a diglycerol content of from 40 to 50% by weight, methylol compounds, such as, in particular, trimethylolethane, trimethylolpropane, trimethylolbutane, pentaerythritol and dipentaerythritol, lower alkyl glucosides, in particular those having 1 to 4 carbon atoms in the alkyl radical, such as, for example, methyl glucoside and butyl glucoside, sugar alcohols having 5 to 12 carbon atoms, such as, for example, sorbitol or mannitol, sugars having 5 to 12 carbon atoms, such as, for example, glucose or sucrose, amino sugars, such as, for example, glucamine.

Preferably used hydrotropes as liquefying agents are, for example, glycerol, propylene glycol, butylene glycol, polyethylene glycol or polypropylene glycol.

The invention therefore further provides liquid, pumpable emulsifier systems which comprise a liquefying agent as an additional component.

These emulsifier systems are preferably clear to translucent-opaque.

The emulsifier systems according to the invention are used as oil-in-water emulsifiers for the preparation of cosmetic and pharmaceutical oil-in-water emulsions; they can therefore also be used as dispersion auxiliaries for particles and pigments and consequently for the preparation of dispersions.

Suitable particles and pigments to be dispersed are, for example, finely disperse metal oxides and salts, such as, for example, titanium dioxide, zinc oxide, iron oxide, aluminum oxide, cerium oxide, zirconium oxide, silicates (talc), barium sulfate and zinc stearate. The particles should have an average diameter of less than 100 nm, e.g., between 5 nm and 50 nm and in particular between 15 nm and 30 nm. The particles can have a spherical shape, although it is also possible to use those particles which have an ellipsoidal shape or a shape which deviates in some other way from the spherical form. Particles and pigments can moreover be micronized organic pigments, such as, for example, 2,2'-methylenebis{6-(2H-benzotriazol-2-yl)-4-(1,1,3,3-tetramethylbutyl)phenol} with a particle size of <200 nm. Furthermore, particles and pigments which lead to special sensory effects can also be dispersed in, such as, for example, nylon-12, boron nitride, polymer particles such as, for example, polyacrylate or polymethyl acrylate particles or silicone elastomers.

Cosmetic and pharmaceutical oil-in-water emulsions and dispersions comprising emulsifier systems according to the invention are further provided by the invention.

The cosmetic and pharmaceutical emulsions and dispersions according to the invention comprise, based on the total mass, more mass percent of oil component than the sum of the mass percentages of emulsifier, surfactant and optionally coemulsifier.

Emulsifier systems according to the invention are preferably used for producing O/W impregnation emulsions for cosmetic textiles. The textiles are preferably wet wipes, particularly preferably cosmetic wet wipes.

The O/W impregnation emulsions for textiles obtained with the help of the emulsifier systems according to the invention are also provided by the invention.

The textiles impregnated with O/W impregnation emulsions according to the invention are likewise provided by the invention.

These are characterized by a good cleaning performance and a pleasant velvety-smooth skin feel.

The invention further provides the use of the emulsifier systems according to the invention for producing cosmetic, dermatological or pharmaceutical formulations. The cosmetic, dermatological or pharmaceutical formulation comprising at least one emulsifier system according to the invention or at least one emulsion or dispersion according to the invention is thus likewise provided by the invention.

The cosmetic, dermatological or pharmaceutical formulations and also the care and cleansing compositions can, for example, comprise at least one additional component selected from the group of
emollients,
emulsifiers and surfactants,
thickeners/viscosity regulators/stabilizers,
UV photo-protective filters,
antioxidants,
hydrotropes (or polyols),
solids and fillers,
film formers,
pearlescent additives,
deodorant and antiperspirant active ingredients,
insect repellents,
self-tanning agents,
preservatives,
conditioners,
perfumes,
dyes,
cosmetic active ingredients,
care additives,
superfatting agents,
solvents.

Substances which can be used as exemplary representatives of the individual groups can be found in the German application DE 102008001788.4. This patent application is hereby incorporated by reference and thus forms part of the disclosure.

In one preferred embodiment, the cosmetic, dermatological or pharmaceutical formulations according to the invention comprise, as an additional component, particles or pigments, preferably those selected from the group titanium dioxide, zinc oxide, iron oxide, aluminum oxide, zirconium oxide, silicates (talc), and zinc stearate, nylon-12, boron nitride, polyacrylate or polymethyl acrylate particles or silicone elastomers.

In a further preferred embodiment, the cosmetic, dermatological or pharmaceutical formulations according to the invention comprise, as an additional component, cosmetic active ingredients, preferably those selected from the group: tocopherol, tocopherol acetate, tocopherol palmitate, ascorbic acid, deoxyribonucleic acid, coenzyme Q10, retinol, bisabolol, allantoin, phytantriol, panthenol, AHA acids, amino acids, hyaluronic acid, alpha-hydroxy acids, polyglutamic acid, creatine (and creatine derivatives), guanidine (and guanidine derivatives), ceramides, phytosphingosine (and phytosphingosine derivatives), sphingosine (and sphingosine derivatives), pseudoceramides, sphingolipids, essential oils, peptides and oligopeptides, protein hydrolysates, plant extracts and vitamin complexes.

Possible application forms of the emulsions and dispersions comprising the emulsifier system according to the invention are therefore sprays, lotions, creams, and ointments. Consequently the use over a very wide consistency range from water-thin to heavily pasty, in the extreme case even solid, is possible.

The emulsifier systems can therefore be used, for example, in care creams and lotions for face, body and hands, in sunscreen emulsions, in make-up, in aerosols, roll-ons, pump sprays, sticks e.g., in the AP/deo sector, in babycare products, in intimate care products, foot care products, hair care products, nail care products, dental care products or oral care products, and also in dermatological ointments.

In the examples given below, the present invention is described by way of example without any intention to limit the invention to the embodiments given in the examples. The scope of application of the invention arises from the entire description and the claims.

Examples

General scheme 1 for the preparation of the polyethersiloxanes used in the examples:

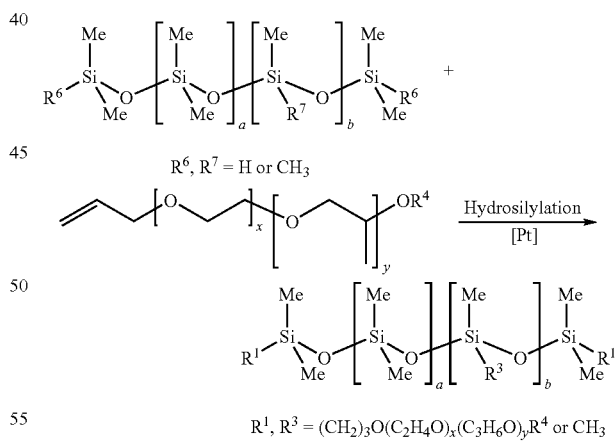

Emulsifier 1:

According to Scheme 1, in a four-neck flask provided with a stirrer, dropping funnel, thermometer and reflux condenser, 48 g (25 mmol of SiH) of an SiH siloxane (where $R^6=R^7=H$, a=200, b=5), 17 g (25 mmol of SiH) of a second SiH siloxane (where $R^6=CH_3$, $R^7=H$, a=80, b=10), 101 g (65 mmol) of an allyl polyether (where x=25, y=4, $R^4=CH_3$) and 10 ppm of Karstedt catalyst in 100 ml of toluene were reacted at 95° C. under nitrogen. According to SiH value determination, complete reaction of the SiH siloxane was obtained after 2 h. Volatile fractions were then distilled off in vacuo at 120° C. A viscous, clear, virtually colorless product was obtained.

Emulsifier 2:

According to Scheme 1, in a four-neck flask provided with a stirrer, dropping funnel, thermometer and reflux condenser, 18 g (10 mmol of SiH) of an SiH siloxane (where $R^6$=H, $R^7$=Me, a=50, b=0), 14 g (20 mmol of SiH) of a second SiH siloxane (where $R^6$=Me, $R^7$=H, a=80, b=10), 63 g (20 mmol of SiH) of a third SiH siloxane (where $R^6$=CH$_3$, $R^7$=H, a=200, b=5), 90 g (65 mmol) of an allyl polyether (where x=20, y=5, $R^4$=H) and 10 ppm of Karstedt catalyst in 50 ml of toluene were reacted at 95° C. under nitrogen. According to SiH value determination, complete reaction of the SiH siloxane was obtained after 2 h. Volatile fractions were then distilled off in vacuo at 120° C. A viscous, cloudy, slightly yellow product was obtained which phase-separated after storage. Prior to use in the emulsion experiments, the product was homogenized by simple stirring at room temperature.

Emulsifier 3:

Product of "Example 3" was obtained by mixing the following polyethersiloxanes prepared individually according to Scheme 1 and analogously to Example 1 in capric/caprylic triglyceride.

50 g of a first polyethersiloxane (where $R^1$=CH$_3$, $R^3$=PE, x=25, y=4, $R^4$=CH$_3$, a=45, b=5) and 32 g of a second polyethersiloxane (where $R^1$=$R^3$=PE, x=20, y=5, $R^4$=H, a=200, b=6) were dissolved in 18 g of capric/caprylic triglyceride.

Emulsifier 4:

Product of "Example 4" was obtained by mixing the following polyethersiloxanes prepared individually according to Scheme 1 and equivalently to Example 1 in capric/caprylic triglyceride.

50 g of a first polyethersiloxane (where $R^1$=CH$_3$, $R^3$=PE, x=25, y=4, $R^4$=CH$_3$, a=45, b=5) and 32 g of a second polyethersiloxane (where $R^1$=$R^3$=PE, x=20, y=5, $R^4$=H, a=200, b=6) were dissolved in 18 g of capric/caprylic triglyceride.

Emulsifier 5:

Product of "Example 5" was obtained by mixing the following polyethersiloxanes prepared individually according to Scheme 1 and equivalently to Example 1 in capric/caprylic triglyceride.

45 g of a first polyethersiloxane (where $R^1$=CH$_3$, $R^3$=PE, x=25, y=4, $R^4$=CH$_3$, a=45, b=5), 28 g of a second polyethersiloxane (where $R^1$=$R^3$=PE, x=20, y=5, $R^4$=H, a=200, b=6) and 11 g of a polyethersiloxane with the following structure $$[R^9Me_2SiO_{1/2}]_3[SiMe_2O_{2/2}]_{50}[SiPhO_{3/2}]$$

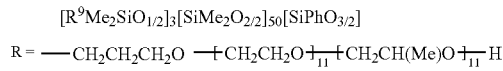

were dissolved in 16 g of capric/caprylic triglyceride.

GPC data for the emulsifier examples:

| Emulsifier | D | Fraction > $10^4$ g/mol | Fraction > $10^5$ g/mol |
|---|---|---|---|
| 1 | 1.8 | 92.2% | 5.3% |
| 2 | 2.1 | 86.4% | 2.5% |
| 3 | 1.8 | 86.4% | 2.5% |
| 4 | 1.8 | 88.8% | 3.9% |
| 5 | 1.9 | 83.8% | 2.7% |

Comparison Emulsifiers CE1-4 (Not According to the Invention, For Delimitation from the Prior Art):

The structures of comparison emulsifiers CE1 to CE3 correspond to the following general formula:

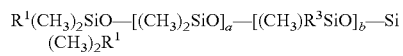

where: $R^1$, $R^3$=CH$_3$ or a polyether ("PE") of the type:

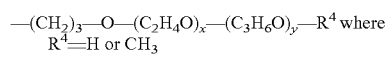

| Comp. emul-sifier | a | b | $R^1$ | $R^3$ | $R^4$ | x | y | D | Fraction >$10^4$ g/mol | Fraction >$10^5$ g/mol |
|---|---|---|---|---|---|---|---|---|---|---|
| CE1 | 50 | 0 | PE | — | CH$_3$ | 15 | 10 | 1.3 | 31.0% | <0.1% |
| CE2 | 100 | 0 | PE | — | H | 11 | 17 | 1.3 | 62.7% | <0.1% |
| CE3 | 20 | 5 | CH$_3$ | PE | H | 14 | 4 | 1.5 | 58.1% | <0.1% |

Comparison emulsifiers CE1-2 correspond to Examples 2-3 of EP 1125574.

Comparison emulsifier CE3 is a typical polyethersiloxane with a comb-like structure.

Comparison Emulsifier CE4:

ABIL CARE 85 (INCI: Bis-PEG/PPG-16/16 PEG/PPG-16/16 Dimethicone; Caprylic/Capric Triglyceride; EVONIK Goldschmidt GmbH):

D=1.4;

Fraction>$10^4$ g/mol=58.4%;

Fraction>$10^5$ g/mol=<0.1%.

Application Examples

All of the concentrations in the application examples are given in percent by weight. To prepare the emulsions, customary homogenization processes known to one skilled in the art were used.

Emulsifying Power.

To investigate the emulsifying power in O/W emulsions, a quick test was used which, under very critical conditions (only 0.5% emulsifier), very rapidly shows which emulsifier systems are characterized by excellent emulsifying activity.

Using customary oils and stabilizers, in particular the stability after storage for 24 h at 50° C. shows very clearly whether an emulsifier system had very good stabilizing properties.

In Table 1 the results of the emulsifier systems 1 to 5 according to the invention are summarized compared to the results of comparison emulsifiers CE1 to CE4.

The emulsions were prepared here by the following process:

Phases A and B were mixed at room temperature, phase C was added without stirring. The mixture was then homogenized for 1 min. Phases D and E were added, then the mixture was homogenized again for 1 min.

The results of Emulsion Examples 1 to 5 show that the emulsifiers according to the invention have considerably higher stabilization properties than the comparison emulsifiers CE1-4.

TABLE 1

Composition and assessment of the investigations in the emulsion quick test.

|   |   | _____ Examples _____ ||||| 
|---|---|---|---|---|---|---|
|   |   | 1 | 2 | 3 | 4 | 5 |
| A | Emulsifier system 1 | 0.5% |  |  |  |  |
|   | Emulsifier system 2 |  | 0.5% |  |  |  |
|   | Emulsifier system 3 |  |  | 0.5% |  |  |
|   | Emulsifier system 4 |  |  |  | 0.5% |  |
|   | Emulsifier system 5 |  |  |  |  | 0.5% |
|   | Ethylhexyl Stearate | 9.0% | 9.0% | 9.0% | 9.0% | 9.0% |
|   | Paraffinum Perliquidum | 9.0% | 9.0% | 9.0% | 9.0% | 9.0% |
|   | Ethanol | 5.0% | 5.0% | 5.0% | 5.0% | 5.0% |
| B | Carbomer | 0.16% | 0.16% | 0.16% | 0.16% | 0.16% |
|   | Ethylhexyl Stearate | 1.04% | 1.04% | 1.04% | 1.04% | 1.04% |
| C | Demineralized Water | ad 100% | ad 100% | ad 100% | ad 100% | ad 100% |
| D | NaOH (5% solution) | 1.25% | 1.25% | 1.25% | 1.25% | 1.25% |
| E | Euxyl ® K 300[1)] | 0.70% | 0.70% | 0.70% | 0.70% | 0.70% |
|   | Stability after 24 h at 50° C. | stable | stable | stable | stable | stable |

[1)]Euxyl ® K 300(Schülke & Mayr): Phenoxyethanol, Methylparaben, Ethylparaben, Propylparaben, Butylparaben, Isopropylparaben Comparative Examples

|   |   | _____ Examples _____ |||| 
|---|---|---|---|---|---|
|   |   | C1 | C2 | C3 | C4 |
| A | Comparison emulsifier CE1 | 0.5% |  |  |  |
|   | Comparison emulsifier CE2 |  | 0.5% |  |  |
|   | Comparison emulsifier CE3 |  |  | 0.5% |  |
|   | Comparison emulsifier CE4 |  |  |  | 0.5% |
|   | Ethylhexyl Stearate | 9.0% | 9.0% | 9.0% | 9.0% |
|   | Paraffinum Perliquidum | 9.0% | 9.0% | 9.0% | 9.0% |
|   | Ethanol | 5.0% | 5.0% | 5.0% | 5.0% |
| B | Carbomer | 0.16% | 0.16% | 0.16% | 0.16% |
|   | Ethylhexyl Stearate | 1.04% | 1.04% | 1.04% | 1.04% |
| C | Demineralized Water | ad 100% | ad 100% | ad 100% | ad 100% |
| D | NaOH (5% solution) | 1.25% | 1.25% | 1.25% | 1.25% |
| E | Euxyl ® K 300 | 0.70% | 0.70% | 0.70% | 0.70% |
|   | Stability after 24 h at 50° C. | Oil separation, severe coalescence | Oil separation, severe coalescence | severe coalescence | Oil separation, severe coalescence |

Skin Feel and Emulsion Stability:

In order to investigate skin feel and stability of the two emulsifier systems 1 and 2 according to the invention, these were used in a concentration of 2% in a cosmetic formulation (Emulsion Examples 6 and 7).

The comparative examples used were the comparison emulsifiers CE1 to CE4. (Comparison Emulsion Examples C5 C8).

The skin feel of the corresponding emulsion was assessed in a panel of 10 people compared in each case to the formulation with comparison emulsifier CE1.

The test results are summarized in Table 2.

The emulsion samples were stored for assessment at room temperature, 5° C., 40° C., and 45° C. and assessed after a storage time of three months.

Since primarily the storage at 45° C. is particularly critical, the stability data in Table 2 are limited to the observations at 45° C.

In these example formulations, it becomes clear that only with the emulsifiers according to the invention is it possible to prepare formulations which are both stable and also advantageous in regard to skin feel.

TABLE 2

Skin feel and stability data of test emulsions

| | Examples | | | | | |
|---|---|---|---|---|---|---|
| | 6 | 7 | C5 | C6 | C7 | C8 |
| Emulsifier system 1 | 2.00% | | | | | |
| Emulsifier system 2 | | 2.00% | | | | |
| Comparison emulsifier CE1 | | | 2.00% | | | |
| Comparison emulsifier CE2 | | | | 2.00% | | |
| Comparison emulsifier CE3 | | | | | 2.00% | |
| Comparison emulsifier CE4 | | | | | | 2.00% |
| Ethylhexyl Stearate | 10.0% | 10.0% | 10.0% | 10.0% | 10.0% | 10.0% |
| Paraffinum Perliquidum | 9.0% | 9.0% | 9.0% | 9.0% | 9.0% | 9.0% |
| Carbomer | 0.16% | 0.16% | 0.16% | 0.16% | 0.16% | 0.16% |
| Xanthan Gum | 0.16% | 0.16% | 0.16% | 0.16% | 0.16% | 0.16% |
| Demineralized Water | ad 100% | ad 100% | ad 100% | ad 100% | ad 100% | ad 100% |
| NaOH (5% solution) | 1.25% | 1.25% | 1.25% | 1.25% | 1.25% | 1.25% |
| Euxyl ® K 300 | 0.70% | 0.70% | 0.70% | 0.70% | 0.70% | 0.70% |
| Stability after 3 months at 45° C. | stable | stable | Oil separation, severe coalescence | Oil separation, severe coalescence | severe coalescence | severe coalescence |
| Skin feel | smooth, velvety | soft, silky, smooth | soft, smooth | soft, smooth, somewhat oily | dry, sticky | soft, smooth, velvety |

Further Emulsion Examples

These examples are intended to show that the emulsifiers according to the invention can be used in a large number of cosmetic formulations.

Moreover, with the help of the emulsifiers according to the invention, it is possible to stably incorporate pigments or solids into formulations.

Furthermore, the examples exhibit good compatibility with typical coemulsifiers, oils, thickeners and stabilizers.

O/W Emulsion Examples

Anti-Aging Day Cream

| | Example 8 |
|---|---|
| Emulsifier system 1 | 1.50% |
| Ceteareth-25 | 1.00% |
| Stearyl Alcohol | 1.50% |
| Glyceryl Stearate | 3.00% |
| Stearic Acid | 1.50% |
| Myristyl Myristate | 1.00% |
| Ceramide IIIB | 0.10% |
| Caprylic/Capric Triglyceride | 5.00% |
| Ethylhexyl Palmitate | 4.40% |
| Ethylhexyl Methoxycinnamate | 2.00% |
| Butyl Methoxydibenzoyl-methane | 1.00% |
| Glycerol | 3.00% |
| Water | ad 100% |

-continued

| | Example 8 |
|---|---|
| TEGO ® Carbomer 134 (Carbomer) | 0.10% |
| Ethylhexyl Palmitate | 0.40% |
| Sodium Hydroxide (10% in water) | q.s. |
| Preservative | q.s. |
| Perfume | q.s. |

Self-Tanning Body Lotion

| | Example 9 |
|---|---|
| Emulsifier system 3 | 2.00% |
| Cetearyl Isononanoate | 5.00% |
| Decyl Cocoate | 5.00% |
| Isopropyl Myristate | 5.00% |
| Sepigel ® Polyacryl-amide; C13-14 Isoparaffin; Laureth-7) | 1.50% |
| PEG-30 Glyceryl Stearate | 2.00% |
| Dihydroxyacetone | 5.00% |
| Propylene Glycol | 3.00% |
| Water | ad 100% |
| Citric Acid | q.s. |
| Preservative | q.s. |
| Perfume | q.s. |

Cationic Sunscreen Cream

|  | Example 10 |
| --- | --- |
| Emulsifier system 2 | 2.00% |
| Distearyldimonium Chloride | 1.50% |
| Glyceryl Stearate | 2.00% |
| Stearyl Alcohol | 1.00% |
| C12-15 Alkyl Benzoate | 5.00% |
| TEGO ® Sun TDEC 45 (Titanium Dioxide; Diethylhexyl Carbonate; Polyglyceryl-6 Polyhydroxy-stearate) | 5.00% |
| Diethylhexyl Carbonate | 3.50% |
| Cetyl Ricinoleate | 1.00% |
| Triisostearin | 1.00% |
| Octocrylene | 3.00% |
| Ethylhexyl Methoxycinnamate | 4.00% |
| Butyl Methoxydibenzoylmethane | 2.00% |
| Water | ad 100% |
| Glycerol | 3.00% |
| Preservative | q.s. |
| Perfume | q.s. |

Skin-Smoothing Body Lotion

|  | Example 11 |
| --- | --- |
| Emulsifier system 5 | 2.50% |
| Diethylhexyl Carbonate | 7.00% |
| Isopropyl Palmitate | 7.60% |
| Creatine | 0.50% |
| Panthenol | 0.50% |
| Glycerol | 3.00% |
| Water | ad 100% |
| TEGO ® Carbomer 341 ER (Acrylates/C10-30 Alkyl Acrylate Cross-polymer) | 0.30% |
| Xanthan Gum | 0.10% |
| Sodium Hydroxide (10% in water) | q.s. |
| TEGO ® Smooth Complex (Betaine; Urea; Potassium Lactate; Polyglutamic Acid; Hydrolyzed Sclerotium Gum) | 2.00% |
| Preservative | q.s. |
| Perfume | q.s. |

Silky Cream Gel

|  | Example 12 |
| --- | --- |
| Emulsifier system 3 | 2.00% |
| Bis-PEG/PPG-14/14 Dimethicone | 2.00% |
| Cyclomethicone | 10.00% |
| Dimethicone | 3.00% |
| Cetyl Ricinoleate | 2.00% |
| Xanthan Gum | 0.20% |
| TEGO ® Carbomer 341 ER (Acrylates/C10-30 Alkyl Acrylate Cross-polymer) | 0.40% |
| Caprylic/Capric Triglyceride | 1.90% |
| Water | ad 100% |
| PEG/PPG-20/20 Dimethicone | 1.00% |
| Alcohol | 5.00% |
| Sodium Hydroxide (10% in water) | q.s. |
| Preservative | q.s. |
| Perfume | q.s. |

O/W Impregnation Emulsion for Cosmetic Wet Wipes

|  |  | Example 13 |
| --- | --- | --- |
| A | TEGO ® Wipe DE (Diethylhexyl Carbonate; Polyglyceryl-4 Laurate; Phenoxyethanol; Methylparaben; Dilauryl Citrate; Ethylparaben; Butylparaben; Propylparaben; Isobutylparaben) | 5.70% |
| B | Demineralized water | 5.70% |
| C | Emulsifier system 1 | 0.30% |
|  | Creatine | 0.25% |
|  | Panthenol | 0.50% |
|  | Demineralized water | 87.55 |
| Z | Perfume | q.s. |

Preparation: At room temperature, firstly A was mixed with B, and then C and Z were added with stirring.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. An emulsifier system for cosmetic and pharmaceutical oil-in-water emulsions comprising at least one high molecular weight organomodified polysiloxane with a polydispersity greater than 1.6, wherein a fraction of the polysiloxanes with a molecular weight of $\geq 1*10^5$ g/mol is above 2%, based on the total amount of the polysiloxane, and wherein the at least one organomodified polysiloxane comprises a polyethersiloxane of general formula I $$M_{2+c+2d}D_aD'_bT_cQ_d \quad \text{formula I,}$$

wherein $M=(R^1R^2{}_2Si\ O_{1/2})$, $D=(R^2, SiO_{2/2})$, $D'=(R^2R^3Si_{2/2})$, $T=(R^2Si\ O_{3/2})$, $Q=(Si\ O_{4/2})$, $a=30-800$, $b=1-15$, $c=0-2$, $d=0-2$, $R^1=R^2$ or $R^3$, $R^2$=independently of one another, identical or different linear or branched, optionally aromatic hydrocarbon radicals having 1 to 16 carbon atoms, which optionally carry OH or ester functions, $R^3$=independently of one another, identical or different polyether radicals of the general formula II $$-CH_2-CH_2-(CH_2)_nO(EO)_x(PO)_y(XO)_zR^4 \quad \text{formula II,}$$

wherein $EO=(C_2H_4O)$, $PO=(C_3H_6O)$, $XO=(C_2H_3R^5O)$, $n=1-9$, $x=2-50$, $y=0-50$, $z=0-10$, $R^4$=independently of one another, identical or different radicals selected from the group consisting of H, alkyl radicals having 1 to 16 carbon atoms, and carboxylate radicals, $R^5$=independently, of one another, identical or different radicals selected from the group consisting of alkyl radicals having 2 to 16 carbon atoms, which are optionally interrupted by ether functions, alkaryl radicals having 7-18 carbon atoms, and aryl radicals having 6 to 16 carbon atoms, and wherein x/(y+z) is >1.

2. The emulsifier system according to claim 1, wherein the fraction of polysiloxanes with a molecular weight of $\geq 1*10^4$ g/mol is above 75%, based on the total amount of the polysiloxane.

3. The emulsifier system according to claim 1, wherein the ratio a/b is >5.

4. The emulsifier system according to claim 1, wherein the polyethersiloxane of general formula I comprises, on average, at least three polyether radicals, and the maximum number of polyether radicals $R^3$ bonded to the molecule is <a/5.

5. The emulsifier system according to claim 1, wherein the polydispersity of the polysiloxane is adjusted by mixing polysiloxanes with different molecular weights.

6. The emulsifier system according to claim 1, wherein the polydispersity of the polyethersiloxane is adjusted by reacting the polyethersiloxane with polyfunctional reactive substrates via the end groups of the polyether.

7. The emulsifier system according to claim 1, wherein the polydispersity of the polysiloxane is adjusted by using polyfunctional double-bond-containing substrates during the preparation of the polysiloxane in the course of the hydrosilylation.

8. A liquid, pumpable emulsifier system according to claim 1, wherein said liquid, pumpable emulsifier system comprises a liquefying agent as an additional component.

9. A cosmetic, dermatological or pharmaceutical oil-in-water emulsion or dispersion including at least the emulsifier system according to claim 1.

* * * * *